(12) United States Patent
Lee et al.

(10) Patent No.: US 8,258,299 B2
(45) Date of Patent: Sep. 4, 2012

(54) PROCESS FOR PREPARATION OF TEMSIROLIMUS

(75) Inventors: Kwang-Chung Lee, Su-Lin (TW); Ting-Huei Lee, Su-Lin (TW); Yen-Shih Tung, Su-Lin (TW); Chia-Chen Kao, Su-Lin (TW); Tzu-Ai Lee, Su-Lin (TW)

(73) Assignee: Chungwa Chemical Synthesis & Biotech Co., Ltd., New Taipei (TW)

( * ) Notice: Subject to any disclaimer, the term of this patent is extended or adjusted under 35 U.S.C. 154(b) by 289 days.

(21) Appl. No.: 12/661,928

(22) Filed: Mar. 29, 2010

(65) Prior Publication Data

US 2010/0249415 A1 Sep. 30, 2010

(30) Foreign Application Priority Data

Mar. 27, 2009 (TW) ................ 98110170 A

(51) Int. Cl.
*C07D 491/12* (2006.01)
*C07D 498/12* (2006.01)
(52) U.S. Cl. ............. 546/90; 540/456; 514/291
(58) Field of Classification Search ........... 540/456, 540/452; 546/90; 514/291
See application file for complete search history.

(56) References Cited

U.S. PATENT DOCUMENTS 6,277,983 B1 * 8/2001 Shaw et al. ............. 540/456
7,097,856 B2 * 8/2006 Frechet et al. ............. 424/486

OTHER PUBLICATIONS

Dorwald F. A. Side Reactions in Organic Synthesis, 2005, Wiley: VCH, Weinheim p. IX of Preface.*

* cited by examiner

*Primary Examiner* — Rita Desai

(57) ABSTRACT

The present invention provides two synthetic routes for the preparation of Temsirolimus (compound 1b and analog of Temsirolimus 1a). The first route includes the synthesis of CCI-779 by directly reacting rapamycin (4b) or Prolyl-rapamycin (4a) with substituent-2,2-bis(methoxy) propionic acid anhydride(11) in the presence of an organic base, followed by deprotection to give CCI-779 or Proline CCI-779. The second route includes a process involving a reaction of rapamycin-OH-31-sily ether (4d) or Prolyl-rapamycin-OH-31-sily ether (4c) with substituent-2,2-bis(methoxy) propionic acid anhydride(11) in the presence of an organic base and followed by subsequent hydrolysis step to obtain the desired CCI-779 or Proline CCI-779.

Compound 11, as described in this invention, is stable at room temperature, cost effective and ease of processing.

7 Claims, No Drawings

PROCESS FOR PREPARATION OF TEMSIROLIMUS

BACKGROUND OF THE INVENTION

1. Field of the Invention

This invention relates to a synthesis of CCI-779 or Proline CCI-779 (Temsirolimus) which is useful as an antineoplastic agent having the structure

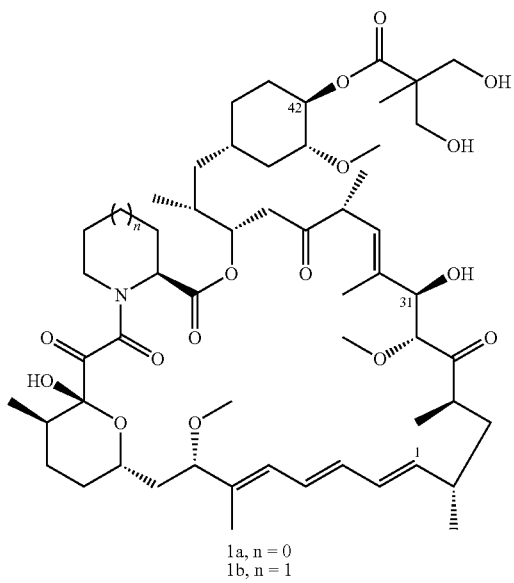

1a, n = 0
1b, n = 1

It is stated to be effective in multiple applications, including inhibition of tumor growth, the treatment for multiple sclerosis and rheumatoid arthritis.

2. The Prior Arts

U.S. Pat. No. 7,202,256 disclosed methods for the synthesis of CCI-779 (Temsirolimus), providing two-step enzymatic process involving regiospecific acylation of rapamycin, using a microbial lipase and an activated ester derivative of 2,2-bis(hydroxymethyl)propionic acid in an organic solvent, followed by deprotection to obtain the CCI-779 (as shown in scheme 1). A number of drawbacks of the synthesis route depicted in scheme 1 are high-priced $PdCl_2$ and poisonous trimethylboroxine.

Scheme 1

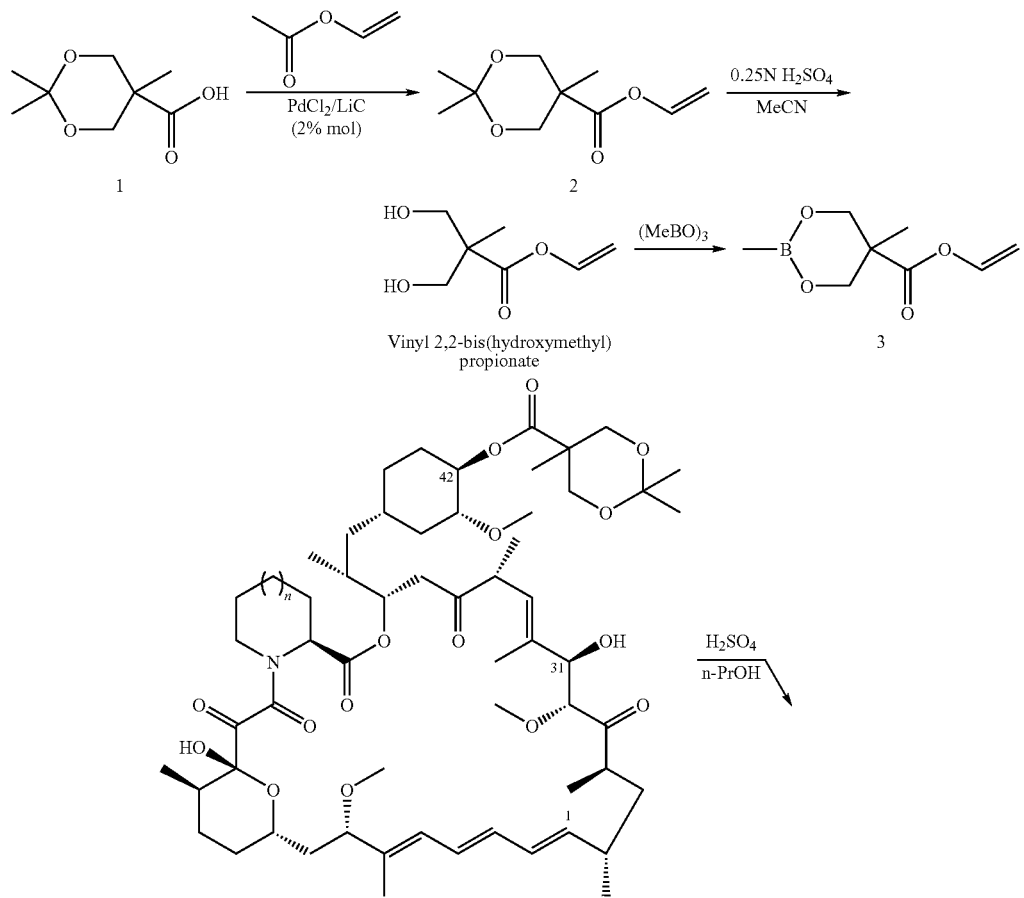

-continued

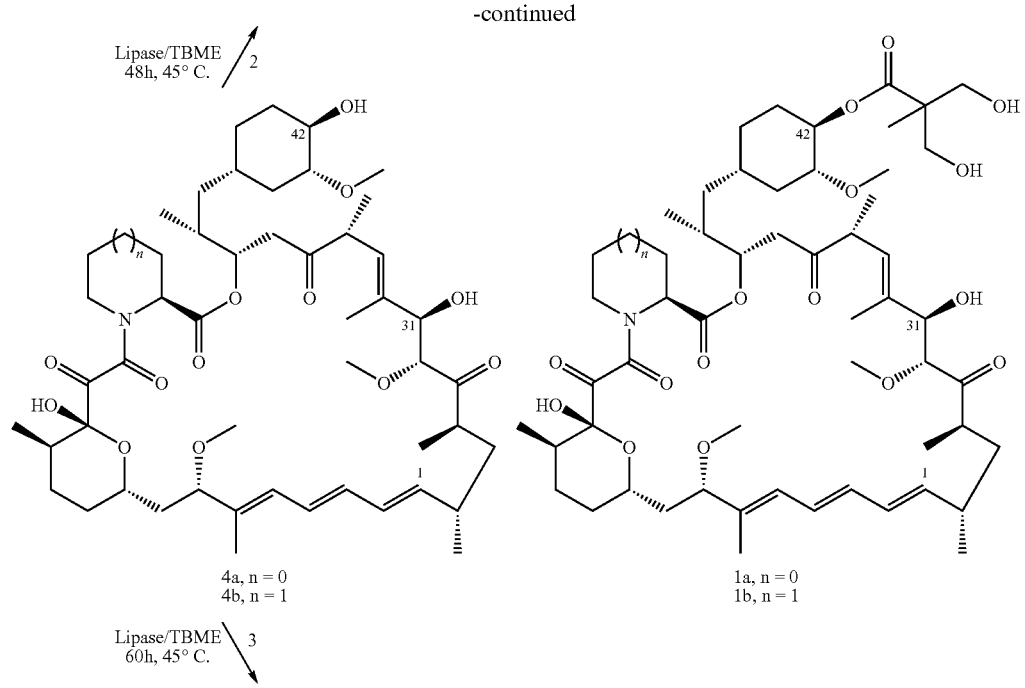

4a, n = 0
4b, n = 1

1a, n = 0
1b, n = 1

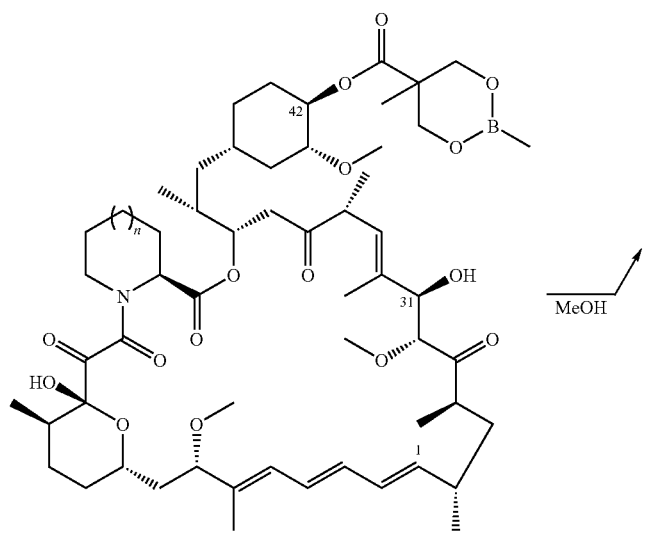

A selective synthesis of 42-monoacylated product was previously conducted by reacting rapamycin 31,42-bis-silyl ether, and then the 42-sily ether protection group is selectively removed to provide rapamycin-OH-31-sily ether (U.S. Pat. No. 5,563,145). In addition, a regioselective process for the preparation of CCI-779 is also described in U.S. Pat. No. 6,277,983 (Scheme2). First, rapamycin (compound 4b) is treated with excess chlorotrimethylsilane to form rapamycin31,42-bis-trimethylsilyl ether (compound 5), and then 42-trimethylsilyl ether protection group is selectively removed in mild acid to provide rapamycin 42-OH-31-trimethylsilyl ether (compound 6). This free 42-OH was then acylated with 2,4,6-trichlorobenzyl mixed anhydride of 2,2,5-trimethyl[1,3-dioxane]-5-carboxylic acid (compound 7) at −15° C. for 16 h to give rapamycin 31-trimethylsilyl ether 42-ester (compound 8). Following treatment with mild acid for a certain period, CCI-779 can be isolated. 2,4,6-trichlorobenzyl chloride is irritant, moisture sensitive and costly.

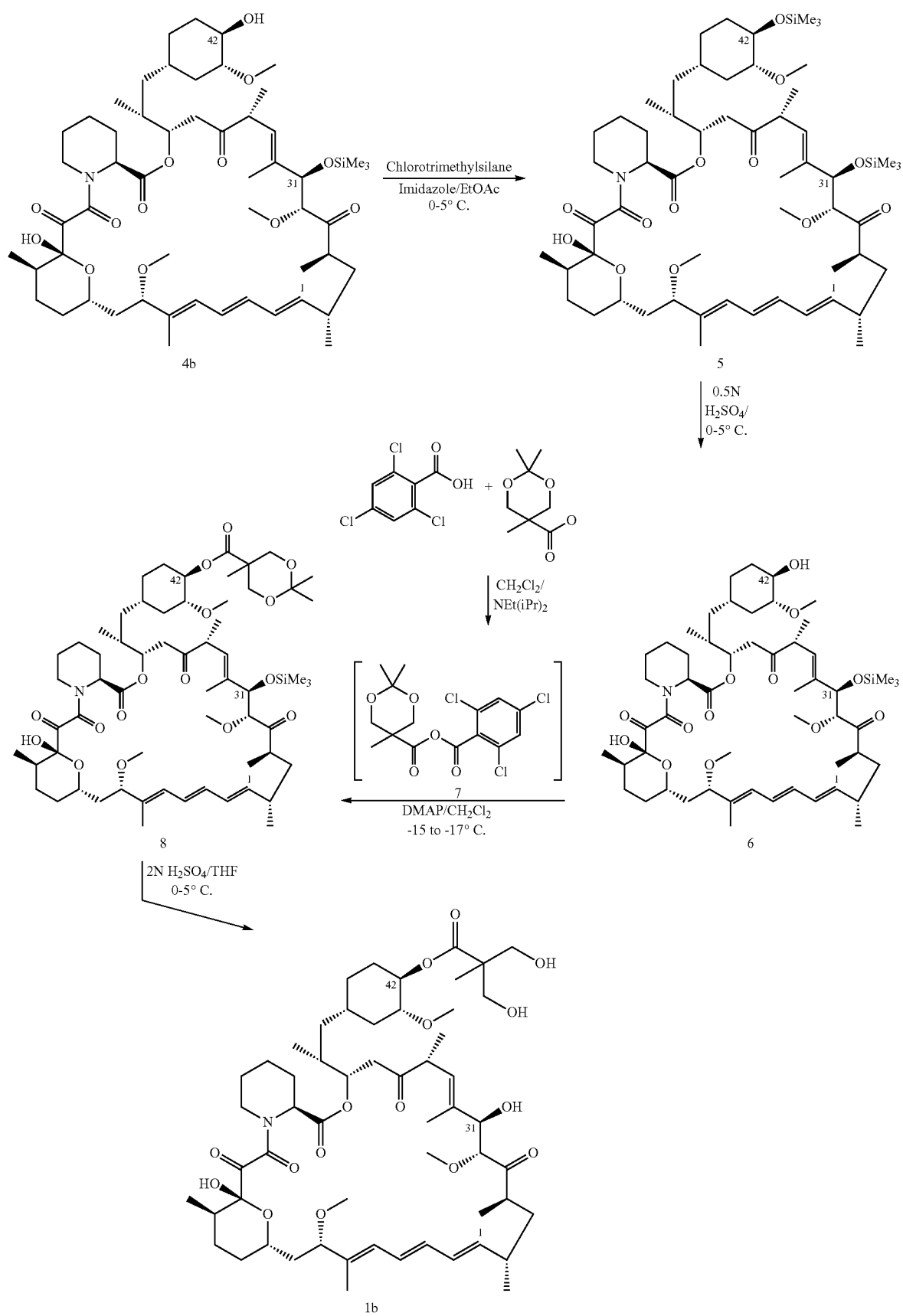

Further, as below-depicted in Scheme 3, U.S. Pat. No. 7,153,957 disclose another method for the CCI-779. It can be prepared by the acylation of 31-silyl ether of rapamycin with the anhydride derived from the 2-phenylboronate acid to give rapamycin 31-silyl ether, 42-boronate. Thereafter, it is hydrolyzed under mild acid condition to form rapamycin 42-ester boronate. After being treated with a suitable diol, CCI-779 was obtained (Scheme 3). Mixed anhydride is not satisfactory for commercial scale synthesis because it can be kept stable only for 48 hr at −5~0° C., not durable for longer time.

The present inventor has found the drawbacks of the prior art and invented the present process for the synthesis of Temsirolimus in a more economic way.

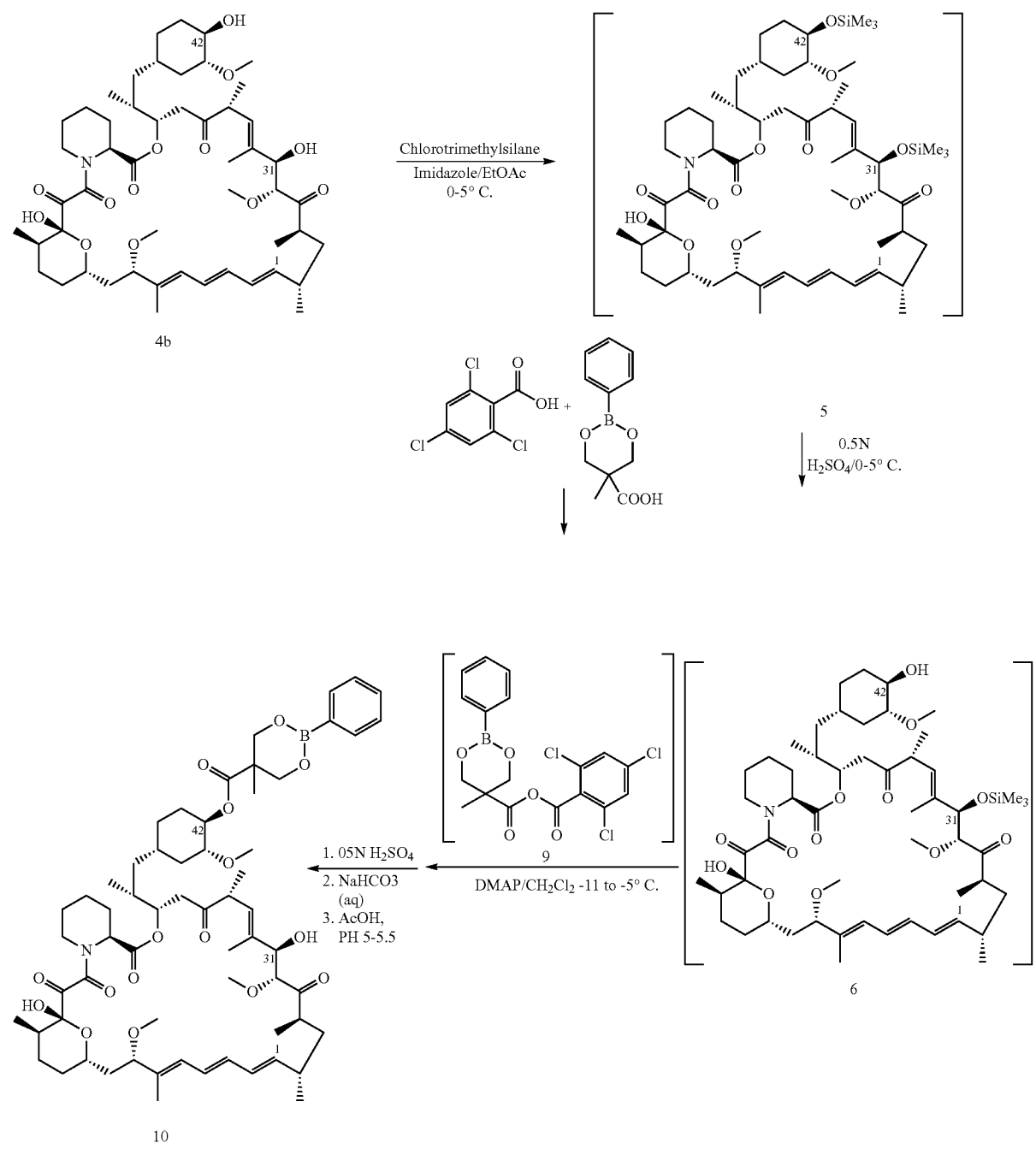

Scheme 3

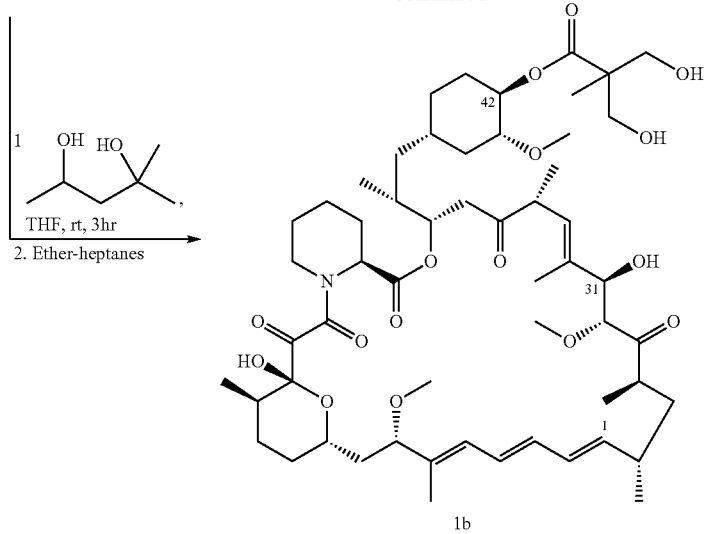

SUMMARY OF THE INVENTION

The object of the present invention is to provide two synthetic routes for the preparation of Temsirolimus (compound 1b and analog of Temsirolimus 1a). The first route includes the synthesis of CCI-779 by directly reacting rapamycin (4b) or Prolyl-rapamycin (4a) with substituent-2,2-bis(methoxy) propionic acid anhydride(11) in the presence of an organic base, followed by deprotection to give CCI-779 or Proline CCI-779. The second route includes a process involving a reaction of rapamycin-OH-31-sily ether(4d) or Prolyl-rapamycin-OH-31-sily ether(4c) with substituent-2,2-bis(methoxy) propionic acid anhydride(11) in the presence of an organic base and followed by subsequent hydrolysis step to obtain the desired CCI-779 or Proline CCI-779.

DETAILED DESCRIPTION

This invention discloses two routes for the synthesis of Temsirolimus or its analog (compound 1b, 1a) by a typical process flow chart as shown in Scheme 4:

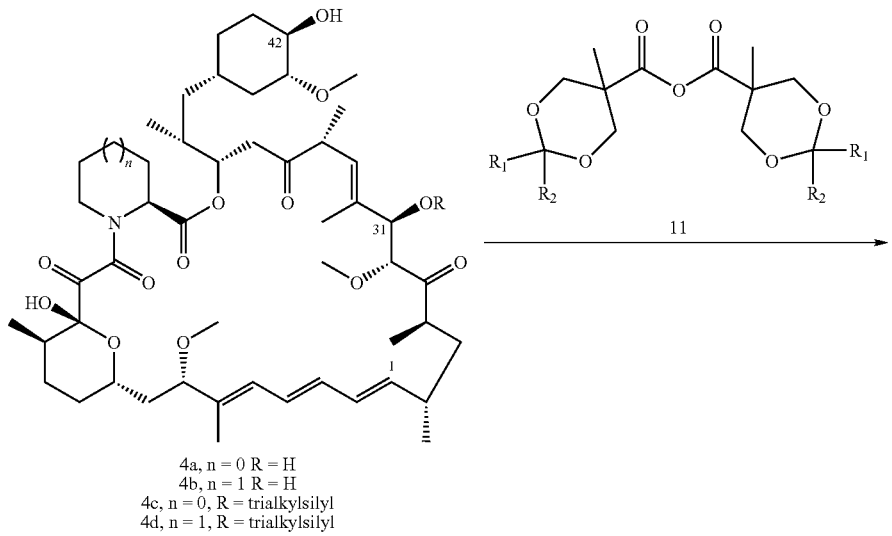

-continued

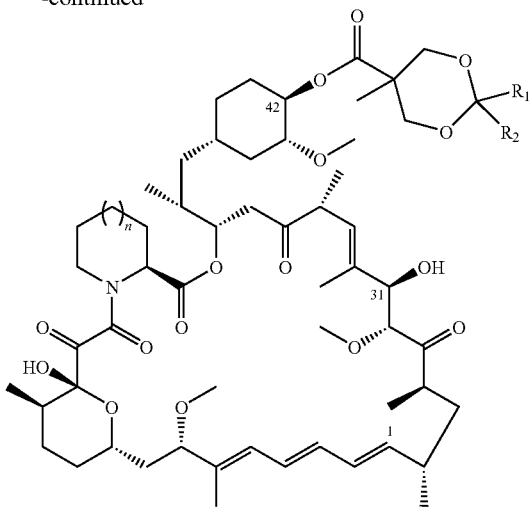

12a, n = 0, R = H
12b, n = 1 R = H
12c, n = 0 R = trialkylsilyl
12d, n = 1 R = trialkylsilyl ↓ Dilute acid

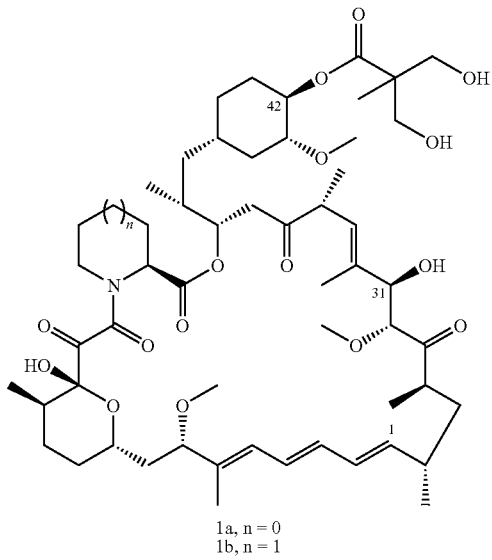

1a, n = 0
1b, n = 1 wherein the reactant 11 is a Substituent-2,2-bis(methoxy) propionic acid anhydride, and the Substituent has a formula of:

wherein $R_1$ or $R_2$ of the substituent is respectively selected from the groups consisting of: hydrogen, alkyl, cycloalkyl, aryl, arylakyl, heteroaryl and heteroarylalkyl. The Substituent may preferably be isopropylidene.

As shown in Scheme 5, a first route for the synthesis of Temsirolimus comprises the reaction of Isopropylidene-2,2-bis(methoxy) propionic acid anhydride (compound 11a) and rapamycin (compound 4b) in the presence of organic base to obtain rapamycin 42-ester of [1,3-dioxane]-5-carboxylic acid (compound 12b). Suitable organic bases can be selected from alkylaminopyridine, pyridine or trialkylamine, etc. However, since rapamycin (compound 4b) contains two secondary hydroxyl groups at positions 31 and 42, it becomes a tough challenge to effectively discriminate these two functional centers in order to achieve a selective synthesis of 42-monoacylated product. Such a reaction produces a 31,42-bis-acylated byproduct and some unreacted rapamycin still remained in the reaction mixture. The longer reaction time, the more degradation by-products are formed. Hence, it requires subsequent column chromatography purification to obtain pure 42-monoacylated product (compound 12b). The deprotection is followed to furnish CCI-779.

SCHEME 5

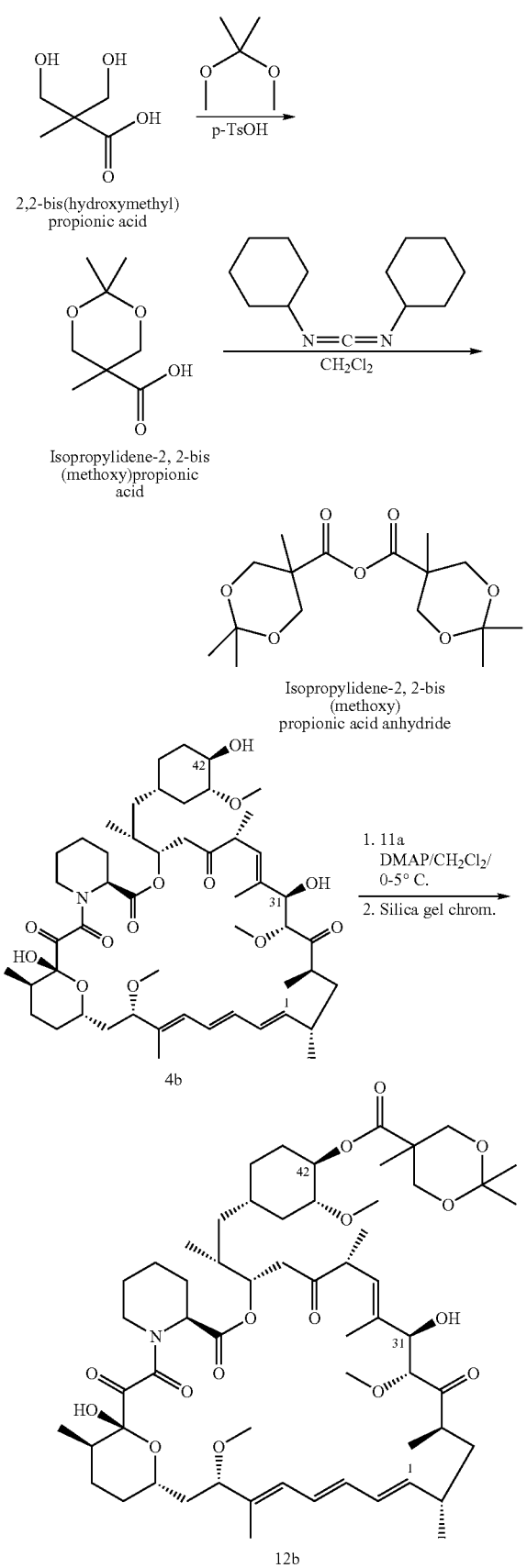

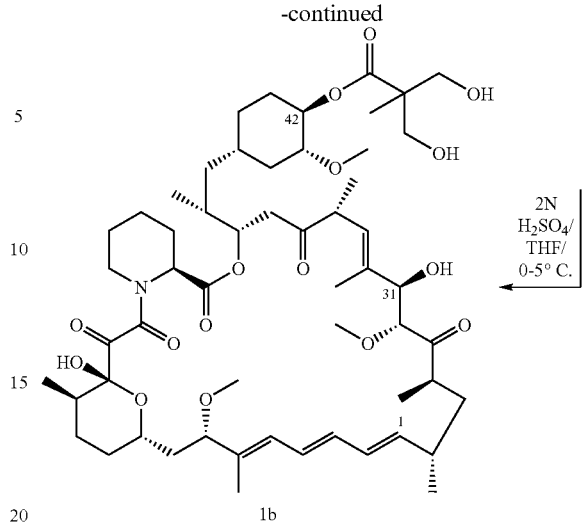

The compound 11a may be used with 0.2~50 equivalents, and is preferably be one equivalent. Reaction temperature may range between –20~30° C. Optimum reaction time is 2~3 hours.

The second route rendering a regioselective synthesis method is shown in below-illustrated Scheme 6.

Firstly, rapamycin 4b is reacted with excess chlorotriethylsilane and imidazole in dichloromethane for two hours to produce compound 14, rapamycin 31,42-bis-triethylsilyl ether (rapamycin 31,42-bis-OTES).

Secondly, the compound 14 is washed by organic solvent and then regioselectively deprotected in the presence of dilute sulfuric acid or dilute acetic acid to produce compound 4d, rapamycin 31-O-triethylsilyl ether.

Thirdly, the compound 4d is treated with Isopropylidene-2,2-bis(methoxy)propionic acid anhydride (compound 11a) in the presence of organic base to obtain ester product 12d, rapamycin 42-ester of 31-O-triethylsilyl ether of 2,2,5-trimethyl[1,3-dioxane]-5-carboxylic acid. Suitable organic bases can be selected from alkylaminopyridine, pyridine or trialkylamine, etc. In the embodiment, the base, 4-dimethylaminopyridine as chosen, will result in a completed reaction in 2~3 hours, under the conditions as described herein.

Fourthly, the ester product 12d is then hydrolyzed with proper quantity of sulfuric acid and deprotected to obtain Compound 1b, Temsirolimus of the present invention. The Compound 11a may be used with 0.2~50 equivalents, and is preferably be five equivalents. Reaction temperature may range between 15~30° C. Optimum reaction time is 2~3 hours.

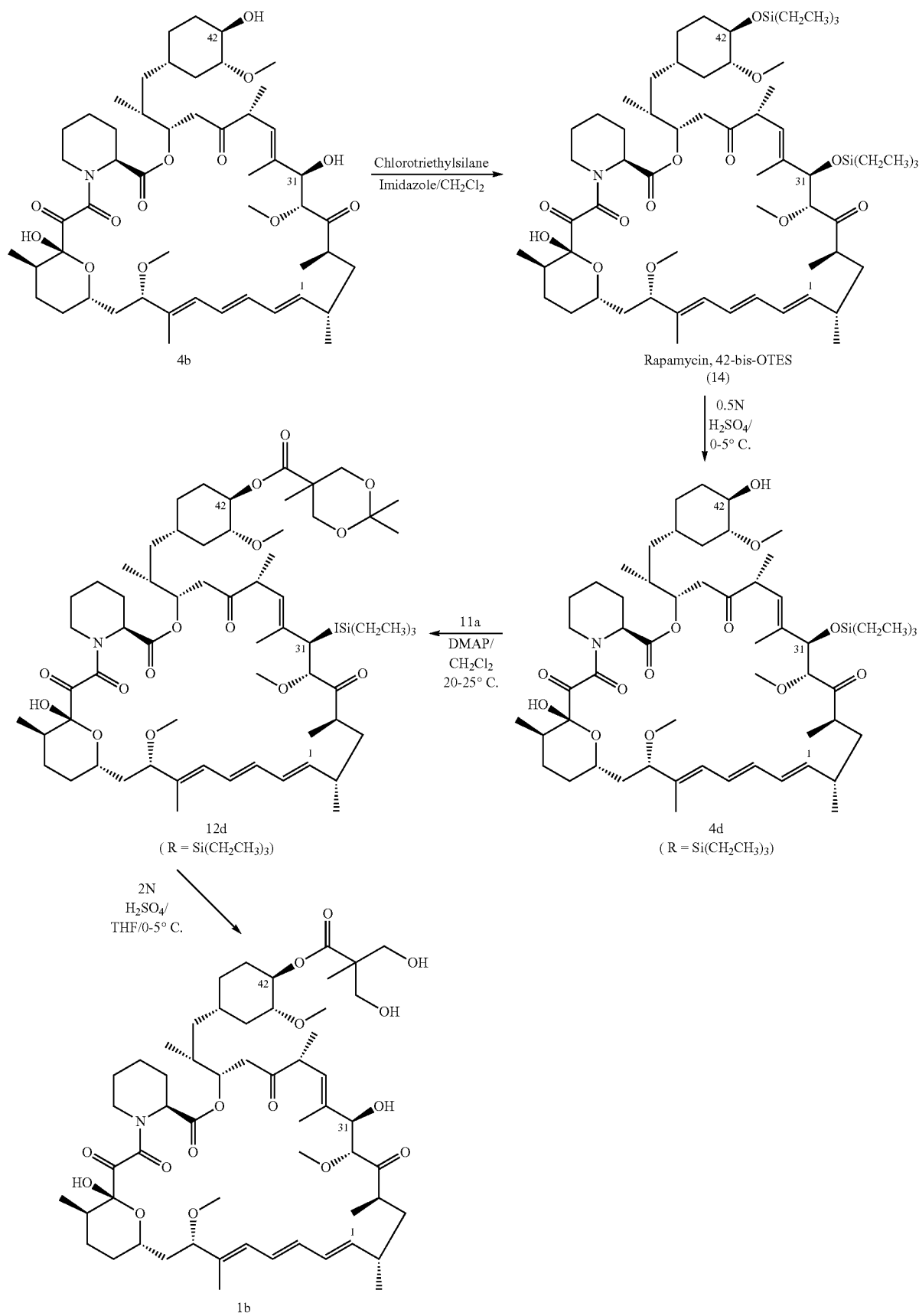

The Temsirolimus as produced by above-mentioned examples is then identified by $^1$H-NMR spectrum which is same as the $^1$H-NMR spectrum as shown in Org. Lett. 2005, 7, 3945-3948.

The present invention has shown its advantages superior to the prior art as follows:
1. The reaction of rapamycin with the Isopropylidene-2,2-bis (methoxy)propionic acid anhydride (compound 11a) only takes 2~3 hours, which is greatly shorter than that as required by the prior arts, thereby saving much time and greatly reducing the production cost.
2. Substituent-2,2-bis(methoxy) propionic acid anhydride (compound 11) as used in the present invention may be stably kept for at least three weeks and its cost is also cheap, thereby helping its inventory control/management and helping reduction of production cost.

Accordingly, the present invention is superior to the prior art, being beneficial for mass production.

The present invention may be further described in detail with reference to the Examples as hereinafter mentioned:

EXAMPLE 1

A. Synthesis of Isopropylidene-2,2-bis(methoxy) propionic acid (Compound 13)

2-2-bis(hydroxymethyl) propionic acid (50.0 g, 372.8 mmol), 2,2-dimethoxypropane (69 ml, 545.4 mmol); p-tolyl-sulfonic acid (3.6 g, 18.7 mmole) and acetone (250 ml) are charged into a reaction flask.

The reaction mixture is agitated at room temperature for two hours, and is dropwise added therein with solution of ammonium hydroxide/ethanol (5 ml, 50/50, v/v). After the dropwise addition, the mixture is further agitated for 10 minutes, concentrated, and added therein with dichloromethane (1250 ml). It is then washed twice with water (100 ml), dried and concentrated to obtain Isopropylidene-2,2-bis(methoxyl) propionic acid, a white solid product (53.6 g), with a yield of 82.6%.

B. Synthesis of Isopropylidene-2,2-bis(methoxy) propionic acid anhydride (Compound 11a)

Isopropylidene-2,2-bis(methoxy) propionic acid (30.0 g, 172.4 mmol) is dissolved in dichloromethane (150 ml). Then, 1,3-dihexylcarbodiimide (17.8 g, 86.3 mmol) is added therein and the reaction is continued at room temperature for 20 hours. N,N-dicyclohexylcarbamide byproduct is filtered off. The reaction product is concentrated to obtain yellow oily product (22.5 g), with a yield of 79.2%.

C. Synthesis of rapamycin 42-ester with 2,2,5-trimethyl[1,3-dioxane]-5-carboxylic acid (Compound 12b, $R_1=R_2=CH_3$)

In a flask, Isopropylidene-2,2-bis(methoxy)propionic acid anhydride (3.7 g, 11.2 mmol) is charged, with nitrogen gas fed therein, and dichloromethane (30 ml) is added. The temperature of reaction mixture is reduced to −5~0° C., and rapamycin (10 g, 10.9 mmol)/dichloromethane (30 ml) is added into the flask. Then, a solution of 4-dimethylaminopyridine (1.4 g, 11.5 mmole)/dichloromethane (15 ml) is slowly dropwise added therein.

After the foregoing dropwise addition, the reaction mixture is heated to 0~5° C. to conduct the reaction for 3 hours. Pure water (70 ml) is added therein and agitated for 5 minutes. Then, it is settled for separating layers. The organic layer is collected and added therein with dichloromethane (130 ml), and then subsequently washed with 0.5N sulfuric acid (130 ml×2), brine (70 ml), saturated sodium bicarbonate solution (70 ml), water (70 ml×2) and brine (70 ml). The washed product mixture is then dried, concentrated to obtain yellow foam solid product (11.8 g). The yellow foam product is purified by silica-gel column chromatography to obtain slightly yellow solid product (3.4 g).

D. Synthesis of Temsirolimus (Compound 1b)

In a flask, rapamycin 42-ester of 2,2,5-trimethyl [1,3-dioxane]-5-carboxylic acid (3.4 g, 3.1 mmol) and tetrahydrofuran (32 ml) are added. The temperature of the reaction mixture is reduced to be 0~5° C. Aqueous solution of sulfuric acid (2N, 9.7 ml) is slowly added dropwise into the flask. The reaction is conducted for 75.5 hours. It is then added with ethyl acetate (70 ml) and brine (14 ml) under agitation.

Then, it is settled for layer separation. The aqueous layer is added with ethyl acetate (14 ml), and agitated for 5 minutes. Again, it is settled for separating layers. All the organic layers are combined and respectively washed with saturated sodium bicarbonate solution (14 ml), water (14 ml×2), and brine (14 ml). After drying and concentrating, a slight yellow solid product (3.0 g) is obtained, with a yield of 26.7% which is calculated based on 5 g of rapamycin.

EXAMPLE 2

A. Synthesis of Rapamycin 31-O-triethylsilyl ether [Compound 4d, $R=Si(CH_2CH_3)_3$]

In a reaction flask, rapamycin (5.0 g, 5.5 mmol) and dichloromethane (75 ml) are added, with nitrogen fed therein, and the temperature of the reaction mixture is reduced to 0~5° C., then added with imidazole (1.5 g, 22.0 mmol), under agitation until completely miscible. Chlorotriethylsilane (3.1 g, 20.2 mmol) is dropwise added therein. After dropwise addition, the reaction mixture is agitated at 0~5° C. for 30 minutes.

It undergoes the reaction at room temperature for 1.5 hours. Then, it is filtered and added with ethyl acetate (160 ml), and further washed with water (81 ml×3) and brine (33 ml). After drying and concentrating, a yellow oily product of rapamycin 31,42-bis-triethylsilyl ether (14) is obtained. Acetone (60 ml) is added and the temperature is reduced to 0~5° C. Aqueous solution of sulfuric acid (0.15N, 15 ml) is added dropwise and the reaction is conducted for one hour. Ethyl acetate (80 ml) is added, and then it is subsequently washed with brine (60 ml×2), saturated sodium bicarbonate solution (40 ml), pure water (60 ml×2) and brine (60 ml). After drying and concentrating, a yellow oily product (8.1 g) is obtained.

B. Synthesis of rapamycin 31-O-triethylsilyl ether, 42 ester with 2,2,5-trimethyl[1,3-dioxane]-5-carboxylic acid [Compound 12d, $R=Si(CH_2CH_3)_3$]

In a reaction flask, isopropylidene-2,2-bis(methoxy) propionic acid anhydride (9.1 g, 27.7 mmole) is added, nitrogen gas fed, and added with dichloromethane (20 ml), rapamycin 31-O-triethylsilyl ether (8.1 g, derived from 5.47 mmol rapamycin)/dichloromethane (10 ml), and dropwise added with 4-dimethylamino pyridine (3.4 g, 27.8 mmol)/dichloromethane (10 ml). After dropwise addition, the mixture is reacted at room temperature for 2 hours.

Water (50 ml) is added and agitated for 5 minutes. It is then settled for layer separation. The organic layer is collected and added with dichloromethane (100 ml). It is then subsequently washed with aqueous solution of sulfuric acid (0.5N, 100 ml×2), brine (50 ml), saturated sodium bicarbonate solution (50 ml), and brine (50 ml). After drying and concentrating, the residue is separated and purified with silica gel column chromatography to obtain yellow oily product (7.2 g).

C. Synthesis of Temsirolimus (Compound 1b)

In a flask, 42-ester (7.2 g, derived from 5.47 mmol rapamycin) from the above step B and tetrahydrofuran (160 ml)

are added. The temperature of the reaction mixture is reduced to 0~5° C. It is then slowly dropwise added with aqueous solution of sulfuric acid (2N, 64.8 ml) for reaction for 50.5 hours. Ethyl acetate (160 ml) and brine (32.5 ml) are added under agitation. Then, it is settled for separating layers. The aqueous layer is added with ethyl acetate (32.5 ml) and agitated for 5 minutes. Then, it is settled. All the organic layers are combined, and respectively washed with saturated sodium bicarbonate solution (26 ml), water (26 ml) and brine (32.5 ml). After drying and concentrating, a slightly yellow solid product (5.3 g) is obtained, with a yield of 93.6% (calculated based on 5 g rapamycin). Then, it is separated and purified by silica gel column chromatography to obtain a white solid product (4.4 g), with a yield of 77.1% (based on 5 g rapamycin).

The foregoing Examples are provided for describing the present invention, but not for limiting the present invention thereto.

The present invention may be further modified without departing from the spirit and scope of the present invention.

The invention claimed is:

1. A process for preparation of Temsirolimus having a structural formula (1) as below-illustrated:

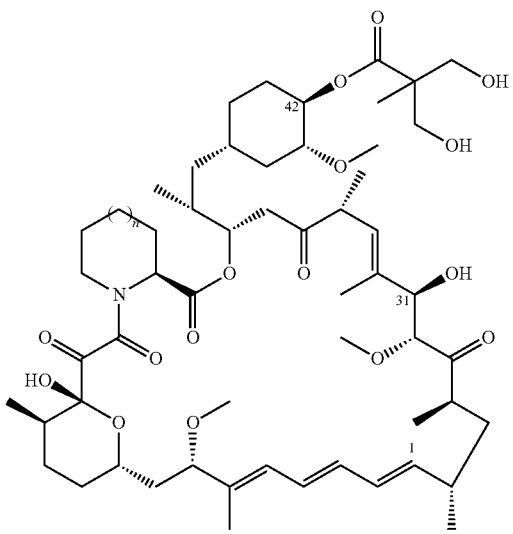

wherein, n=1, the steps comprising: A. acylating the rapamycin (compound 4b)

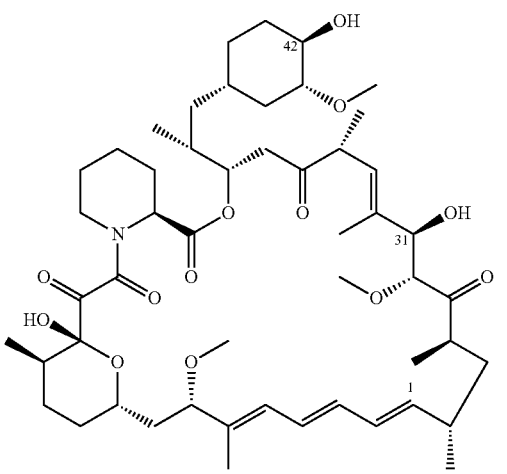

or rapamycin 31-sily ether (compound 4d)

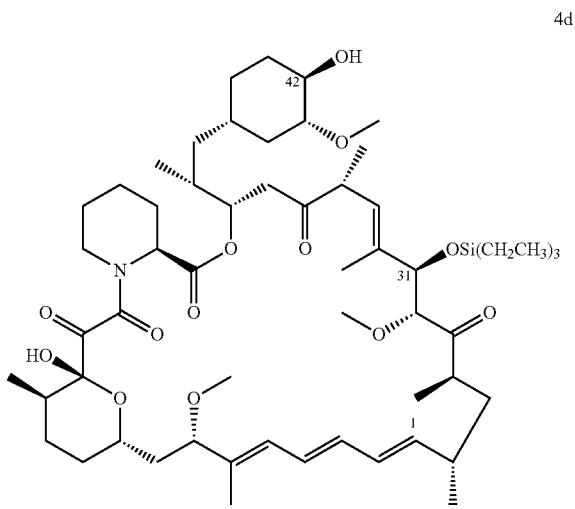

with Isopropylidene-2,2-bis(methoxy)propionic acid anhydride (compound 11a)

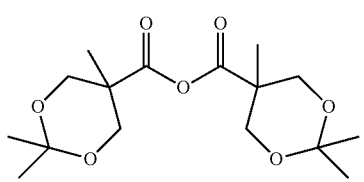

in the presence of organic base to give rapamycin 42-ester of 2,2,5-trialkyl[1,3-dioxane]-5-carboxylic acid (compound 12b)

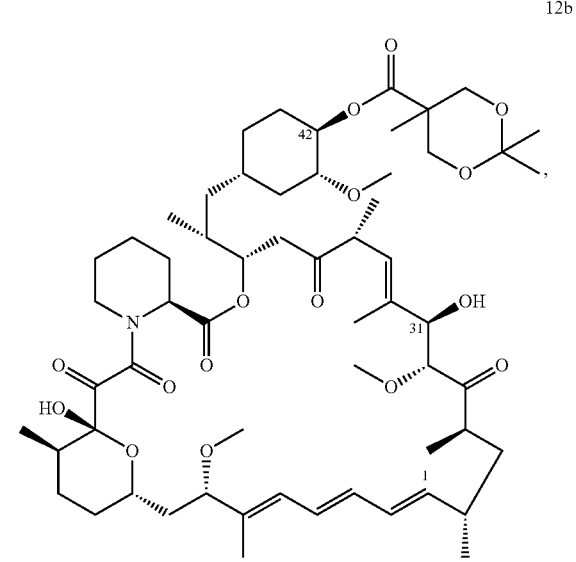

or rapamycin 42-ester of 31-0-trialkylsily ether of 2,2,5-trimethyl[1,3-dioxane]-5-carboxylic acid (compound 12d)

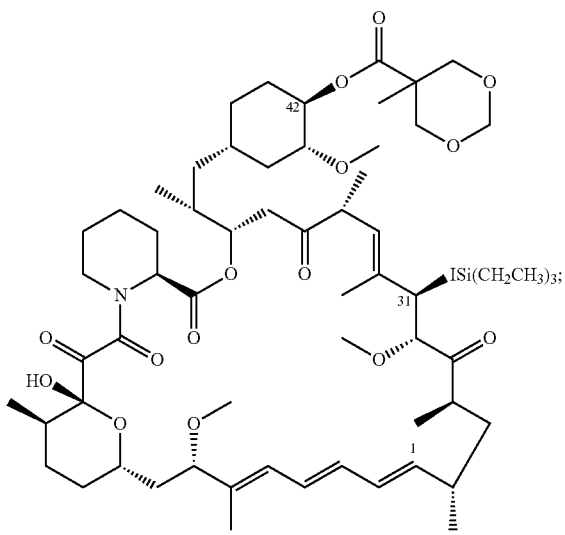

and B. treating said rapamycin 42-ester of 2,2,5-trialkyl[1, 3-dioxane]-5-carboxylic acid (compound 12b), or said rapamycin 42-ester of 31-0-trialkylsily ether of 2,2,5-trimethyl[1,3-dioxane]-5-carboxylic acid (compound 12d) in a mild acidic condition to obtain Temsirolimus.

2. A process according to claim 1, wherein said compound 11 as used has equivalents of 0.2.about.50 times of that of said compound 4b or 4d.

3. A process according to claim 1, wherein said organic base as used has equivalents of 0.2.about.50 times of that of said compound 4b or 4d.

4. A process according to claim 1, wherein acylating said rapamycin (compound 4b) with Isopropylidene-2,2-bis(methoxy)propionic acid anhydride (compound 11a) in said step A is performed at a temperature ranging from −20° C. to about 30° C.

5. A process according to claim 1, wherein acylating said rapamycin 31-sily ether (compound 4d) with Isopropylidene-2,2-bis(methoxy)propionic acid anhydride (compound 11a) in said step A is performed at a temperature ranging from 15° C. to about 30° C.

6. A process according to claim 1, wherein the base in step A includes alkylaminopyridine, pyridine and trialkylamine.

7. A process according to claim 6, wherein the base is 4-dimethylaminopyridine.

* * * * *